US012765951B2

(12) United States Patent
Amat Girbau

(10) Patent No.: US 12,765,951 B2
(45) Date of Patent: Oct. 20, 2026

(54) ADAPTIVE ROBOT-ASSISTED SYSTEM AND METHOD FOR EVALUATING THE POSITION OF THE TROCAR IN A ROBOT-ASSISTED LAPAROSCOPIC SURGERY INTERVENTION

(71) Applicant: Rob Surgical Systems, SL, El Prat de Llobregat (ES)

(72) Inventor: Josep Amat Girbau, Barcelona (ES)

(73) Assignee: Rob Surgical Systems, SL, El Prat de Llobregat (ES)

( * ) Notice: Subject to any disclaimer, the term of this patent is extended or adjusted under 35 U.S.C. 154(b) by 303 days.

(21) Appl. No.: 18/252,384

(22) PCT Filed: Nov. 9, 2021

(86) PCT No.: PCT/EP2021/081052
§ 371 (c)(1),
(2) Date: May 10, 2023

(87) PCT Pub. No.: WO2022/101175
PCT Pub. Date: May 19, 2022

(65) Prior Publication Data
US 2024/0000523 A1 Jan. 4, 2024

(30) Foreign Application Priority Data
Nov. 10, 2020 (EP) .................................... 20382967

(51) Int. Cl.
*A61B 34/20* (2016.01)
*A61B 34/30* (2016.01)

(52) U.S. Cl.
CPC .............. *A61B 34/30* (2016.02); *A61B 34/20* (2016.02); *A61B 2034/2046* (2016.02)

(58) Field of Classification Search
CPC .. A61B 34/30; A61B 34/20; A61B 2034/2046
See application file for complete search history.

(56) References Cited

U.S. PATENT DOCUMENTS 5,855,583 A 1/1999 Wang et al.
8,911,429 B2 * 12/2014 Olds ...................... A61B 90/00 606/1

(Continued)

FOREIGN PATENT DOCUMENTS

EP 3473202 A1 4/2019
JP 2020028645 A 2/2020

(Continued)

OTHER PUBLICATIONS

European Patent Office; International Search Report and Written Opinion for PCT/EP2021/081052; Oct. 2, 2022; entire document.

(Continued)

*Primary Examiner* — Stephen Holwerda
(74) *Attorney, Agent, or Firm* — ALLEN, DYER, DOPPELT + GILCHRIST, P.A.

(57) ABSTRACT

An adaptive robot-assisted system and a method for evaluating the position of the trocar in a robot-assisted laparoscopic surgery intervention are proposed. The system includes a surgical robot with robotic arms, each arm securing, using passive joints, a surgical instrument suitable for being coupled to a trocar. The system also includes a control unit, a command station, and sensors for measuring angles $\alpha$ and $\beta$ of the axes of rotation of the passive joints. The control unit performs a dynamic estimation of the position of a trocar by comparing, for each of the movements of the surgical instrument in the abdominal cavity, the measured angles $\alpha$ and $\beta$ with the theoretical angles $\alpha$ and $\beta$, and performs a correction of or a parameter $\rho$ by positively negatively increasing it in each of said movements according to the sign value of the error obtained in the comparison.

7 Claims, 3 Drawing Sheets

(56) References Cited

U.S. PATENT DOCUMENTS

| | | | | |
|---|---|---|---|---|
| 2007/0013336 | A1* | 1/2007 | Nowlin | A61B 34/30 318/568.21 |
| 2009/0326324 | A1 | 12/2009 | Munoz Martinez et al. | |
| 2014/0052154 | A1* | 2/2014 | Griffiths | B25J 9/1633 606/130 |
| 2015/0351857 | A1* | 12/2015 | Vander Poorten | B25J 18/007 606/130 |
| 2018/0028269 | A1* | 2/2018 | Morel | A61B 34/37 |
| 2019/0117317 | A1* | 4/2019 | Abayazid | A61B 5/066 |
| 2019/0175062 | A1* | 6/2019 | Rafii-Tari | A61B 34/74 |

FOREIGN PATENT DOCUMENTS

| | | |
|---|---|---|
| JP | 2020065644 A | 4/2020 |
| WO | WO0030548 | 6/2000 |

OTHER PUBLICATIONS

Zhang et al.; System Design of a Novel Minimally Invasive Surgical Robot That Combines the Advantages of MIS Techniques and Robotic Technology; IEEE Access; Feb. 27, 2020; pp. 41147-41161.

Darpa; The da Vinci System; Technology and Surgical Analysis; Jun. 9, 2019; Ento Key; https://entokey.com/the-da-vinci-system-technology-and-surgical-analysis/; pp. 1-6.

Ki-Young Kim et al.; Design and evaluation of a slave manipulator with roll-pitch-roll wrist and automatic tool loading mechanism in telerobotic sugery; International Journal of Medical Robotics and Computer Assisted Surgery; Dec. 2012.

* cited by examiner

ADAPTIVE ROBOT-ASSISTED SYSTEM AND METHOD FOR EVALUATING THE POSITION OF THE TROCAR IN A ROBOT-ASSISTED LAPAROSCOPIC SURGERY INTERVENTION

FIELD OF THE INVENTION

The present invention generally relates to the field of laparoscopic surgery. In particular, the invention relates to an adaptive robot-assisted system for evaluating the position of the trocar in a robot-assisted laparoscopic surgery intervention. The invention also provides a method for such purpose.

The proposed system and method allow continuously evaluating the position of each trocar during the intervention, and thus knowing the position of the fulcrum point, i.e., the point of insertion of each trocar in the abdominal wall of the patient. The present invention also allows stabilizing the surgical instruments of the surgical robot when movements occur in the abdominal vault, without the trocar having to be mechanically fixed.

BACKGROUND OF THE INVENTION

The use of robot-assisted laparoscopic surgery began in the late 1980s and it consists of performing a surgical procedure remotely by means of using teleoperated stations connected to a surgical robot.

One of the main problems that applications of this type need to address is the transformation of movements $\vec{M}$ of the command station into movements $\vec{R}$ of the robotic arms, such that the movements of the surgical instruments introduced in the abdominal cavity through the trocar are in accordance with movements $\vec{P}$, which are identical to the mentioned movements $\vec{M}$ of the command station (see FIG. 1).

To prevent surgical instrument instability, the trocar is immobilized on a suitable fulcrum point in space. Nevertheless, if the trocar were to be freely inserted in the abdominal vault, unwanted movements would occur when the trocar changes its position in space, for example, due to the patient's breathing, and the robotic arm driving the surgical instrument would yield given the exerted torque, in this case with an elevation of the abdominal vault.

For the fulcrum point to be invariant throughout the entire operation, most of the current systems use a poly-articulated robotic arm fixing the trocar in space and not allowing the unwanted movement thereof by means of an architecture that allows programming the movements of the different joints, ensuring at all times a remote fixed point for the passage of the shaft of the surgical instrument in all the movements which allow achieving the accessible 3D working volume (Remote Center of Motion, RCM). The position of the surgical instrument in the abdominal cavity therefore no longer depends on a possible movement of the trocar. Nevertheless, the forces applied by robotic arms on the trocar to prevent its movement cause the patient to develop hematomas in some cases, as reflected in the medical literature.

Document [1] describes an architecture characteristic of the preceding strategy. In this architecture, the two rotations J4 and J5 which allow pivoting the surgical instrument about the RCM point mechanically assure the isocentric passage of the surgical instrument since the axes of rotation are aligned with the RCM point.

Document [2] describes a solution similar to the preceding one which is, however, more recent. This document proposes a small table-attached MIS robot that combines the high efficiency of the traditional MIS technique and the dexterity of robotic operations. The master and slave manipulators of the new robot are integrated, which allows the surgeon to manipulate the robot next to the operation table. To reduce the difficulty of operations, especially suturing operations, the surgical instrument is developed with a "roll-pitch-distal roll" wrist and a quick-exchange interface. Likewise, to overcome the uncoordinated hand-eye movement caused by the fulcrum effect, a motion mapping model is established for the robot.

To avoid the side effects typical of a robot-assisted laparoscopic surgery derived from the stresses caused by the trocar on the patient, the introduction of a passive poly-articulated and sensorized arm which allows the actual position of the trocar in the 3D space to be continuously calculated has also been proposed [3]. The system therefore allows ensuring that the surgical robot does not apply any force whatsoever on the trocars, so hematoma development in the patient is prevented. In contrast, the length of penetration of the trocar is not defined, which prevents performing the calculation of the position of the surgical instrument in the abdominal cavity.

In [4], a system for performing minimally invasive cardiac procedures is also disclosed. The system includes a pair of surgical instruments that are coupled to a pair of robotic arms. The instruments have end effectors that can be manipulated to hold and suture tissue. The robotic arms are coupled to a pair of master handles by a controller. The handles can be moved by the surgeon to produce a corresponding movement of the end effectors. The movement of the handles is scaled so that the end effectors have a corresponding movement that is different, typically smaller, than the movement performed by the hands of the surgeon. The scale factor is adjustable so that the surgeon can control the resolution of the end effector movement. The movement of the end effector can be controlled by an input button, so that the end effector only moves when the button is depressed by the surgeon. The input button allows the surgeon to adjust the position of the handles without moving the end effector, so that the handles can be moved to a more comfortable position. The system may also have a robotically controlled endoscope which allows the surgeon to remotely view the surgical site. A cardiac procedure can be performed by making small incisions in the patient's skin and inserting the instruments and endoscope into the patient. The surgeon manipulates the handles and moves the end effectors to perform a cardiac procedure such as a coronary artery bypass graft.

New systems and methods which allow continuously evaluating the position of the trocar when the joints of the robotic arms are passive joints are therefore needed.

REFERENCES

[1] The da Vinci® system: technology and surgical analysis.

[2] System Design of a Novel MIS Robot That Combines the Advantages of MIS Techniques and Robotic Technology, Huaifeng Zhang et al. Digital Object Identifier

[3] Design and evaluation of a slave manipulator with roll-pitch-roll wrist and automatic tool loading mechanism in telerobotic surgery, Ki-Young Kim et al. The International Journal of Medical Robotics and Computer Assisted Surgery.

[4] U.S. Pat. No. 5,855,583 A. Wang Yulun et al. "Method and apparatus for performing minimally invasive cardiac procedures".

DESCRIPTION OF THE INVENTION

To that end, embodiments of the present invention provide according to a first aspect a robot-assisted system susceptible to adaptation (i.e., adaptive) for evaluating the position of the trocar during a robot-assisted laparoscopic surgery intervention. The proposed system comprises a surgical robot equipped with one or more robotic arms poly-articulated with several degrees of freedom. Each robotic arm is arranged/configured for securing, via passive joints, a surgical instrument. Each of the passive joints is configured for rotating freely around a single point of intersection of the axes of rotation.

Likewise, each surgical instrument is arranged/suitable for being coupled to a trocar which can be introduced in the abdominal cavity of a patient during the laparoscopic surgery intervention. The robot-assisted system further includes a control unit configured for controlling movements in the mentioned robotic arms; a command station configured for an assisted/teleoperated manipulation of the surgical robot through control elements; and sensors arranged in each robotic arm and configured for measuring angles of orientation $\alpha$ and $\beta$ of the axes of rotation of the passive joints. The control unit is operatively connected to the command station.

In the proposed system, the mentioned control unit performs a dynamic estimation of the position of one or more of said trocars inserted in the wall of the abdominal cavity by performing a comparison, for each of the movements of the surgical instrument in the abdominal cavity established during a specific time interval during the intervention, of the angles of orientation $\alpha$ and $\beta$ measured by the sensors with the theoretical angles of orientation $\alpha$ and $\beta$ corresponding to an absence of movement of the trocar; and performing a correction of a parameter $\rho$, relative (i.e. that corresponds) to the distance between a point of intersection of the axes of rotation of the passive joints and the corresponding fulcrum point, by positively or negatively increasing said parameter $\rho$ in each of the movements during said specific time interval according to the sign value of the error obtained in the comparison.

In one embodiment, the correction comprises applying a fuzzy logic algorithm.

Particularly, the fuzzy logic algorithm is performed at a speed between about 200 and 1000 times per second. Therefore, due to the need to perform a large number of decisions (positive error or negative error) in each movement, the control unit makes the obtained result a statistical average.

The control unit can be located inside the surgical robot. Alternatively, the control unit can be remote/external with respect to the surgical robot and the command station, and can be connected thereto by means of a cable or wireless connection.

Embodiments of the present invention also provide, according to another aspect, an adaptive method for evaluating the position of the trocar in a robot-assisted laparoscopic surgery intervention. The method comprises performing, using a control unit controlling movements of one or more robotic arms of a surgical robot, a dynamic estimation of the position of a trocar inserted in the abdominal cavity of a patient. The mentioned trocar supports a surgical instrument secured to one of said robotic arms.

To perform the dynamic estimation, the method comprises comparing, for each of the movements of the surgical instrument in the abdominal cavity established during a specific time interval during a laparoscopic surgery intervention, a previously measured angles of orientation $\alpha$ and $\beta$ of the axes of rotation of the passive joints of the robotic arm with the theoretical angles of orientation $\alpha$ and $\beta$ corresponding to an absence of movement of the trocar. Likewise, the method comprises performing correction of a parameter $\rho$, relative/corresponding to a distance between a point of intersection of the axes of rotation of the passive joints and a fulcrum point, by positively or negatively increasing the parameter $\rho$ in each of the movements during the mentioned specific time interval according to the sign value of the error obtained in the comparison, which has been statistically filtered.

In some embodiments, the measured and theoretical angles of orientation $\alpha$ and $\beta$ are stored in a memory or database.

In some embodiments, the method is performed for each of the trocars used during the intervention. Each of the trocars supports a surgical instrument secured to a robotic arm of the surgical robot. In general, each surgical robot includes between 1 and 4 robotic arms.

Other embodiments of the invention disclosed herein may also include computer program products for performing the steps and operations performed by the mentioned control unit.

More particularly, a computer program product is an embodiment comprising a computer system-readable medium including code instructions coded therein which, when executed in at least one processor of the computer system, cause the processor to perform the operations indicated herein as embodiments of the invention.

The present invention therefore allows estimating the position of the trocar/trocars in space by means of recursive calculation taking into consideration the values of the angles of orientation of the instrument of the mentioned passive orienting joints.

BRIEF DESCRIPTION OF THE DRAWINGS

The foregoing and other features and advantages will be better understood based on the following detailed description of several merely illustrative and non-limiting embodiments in reference to the attached drawings in which.

DETAILED DESCRIPTION OF THE INVENTION

The present invention provides an adaptive robot-assisted system, particularly for minimally invasive surgery, and an adaptive method, for evaluating the position of the trocar in a robot-assisted laparoscopic surgery intervention.

The robot-assisted system 1 proposed by the present invention has a configuration which allows for a floating trocar, making the joints about which the trocar pivots passive joints and causing the trocar itself to be responsible for fixing its orientation without the robot-assisted system effecting any resistant torque whatsoever.

Figure 1:
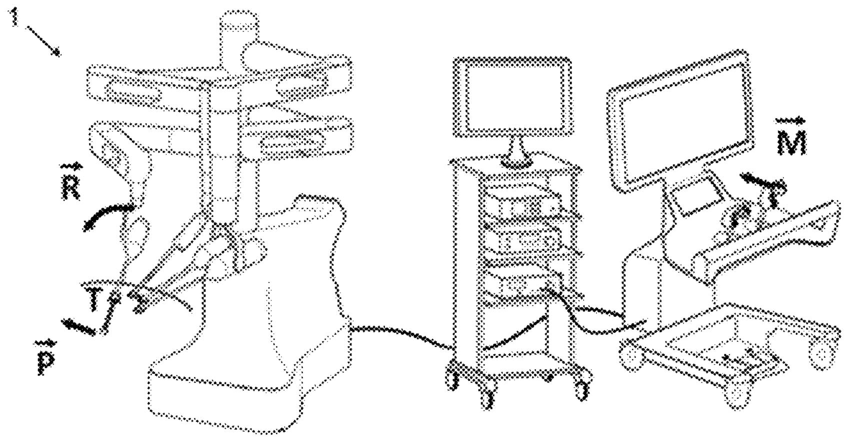
FIGS. 1 and 2 illustrate the architecture of the proposed system, according to embodiments of the present invention.
Figure 2:
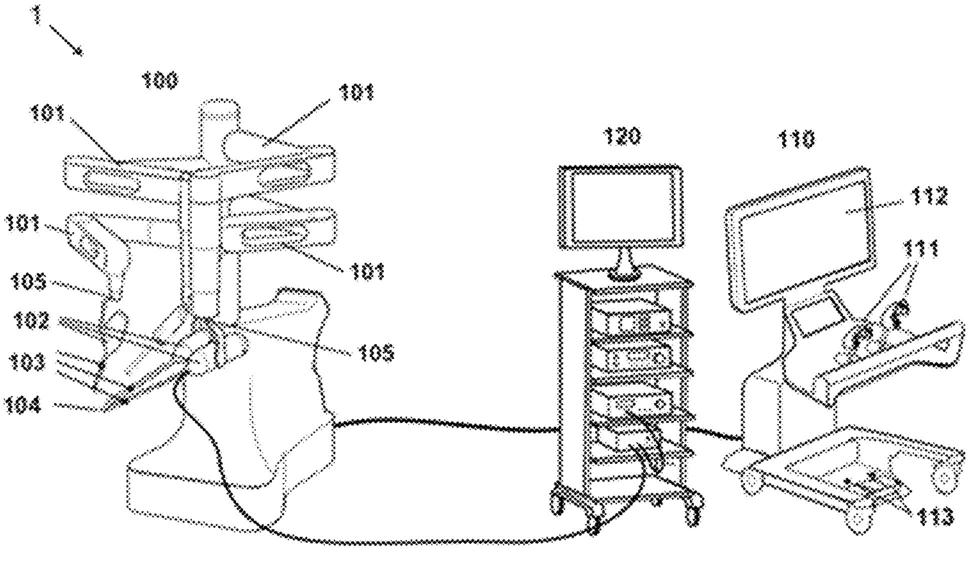

With reference to FIG. 2, therein it is shown an embodiment of the proposed robot-assisted system 1. In this embodiment, the system 1 comprises a surgical robot 100 equipped with four robotic arms 101 each holding and operating a surgical instrument 102 which pivots through a trocar 103. The operator controls the robot from a command station 110 through controls 111 and/or pedals 113, viewing the scene by means of a screen 112. Likewise, the system comprises a control unit (not illustrated) which calculates the movements of the joints of the robotic arms 101 so that the securing points 105 supporting the surgical instruments 102 execute several trajectories, such that the trajectories executed by the distal elements 104 of the surgical instruments 102 pivoting through the trocar 103 correspond with the movements performed by the operator through the controls 111 and/or pedals 113.

The control unit may include a processing unit formed by one or more processors and peripherals, for example an arithmetic logic unit, communication buses, input/output elements, etc.

Figure 3:
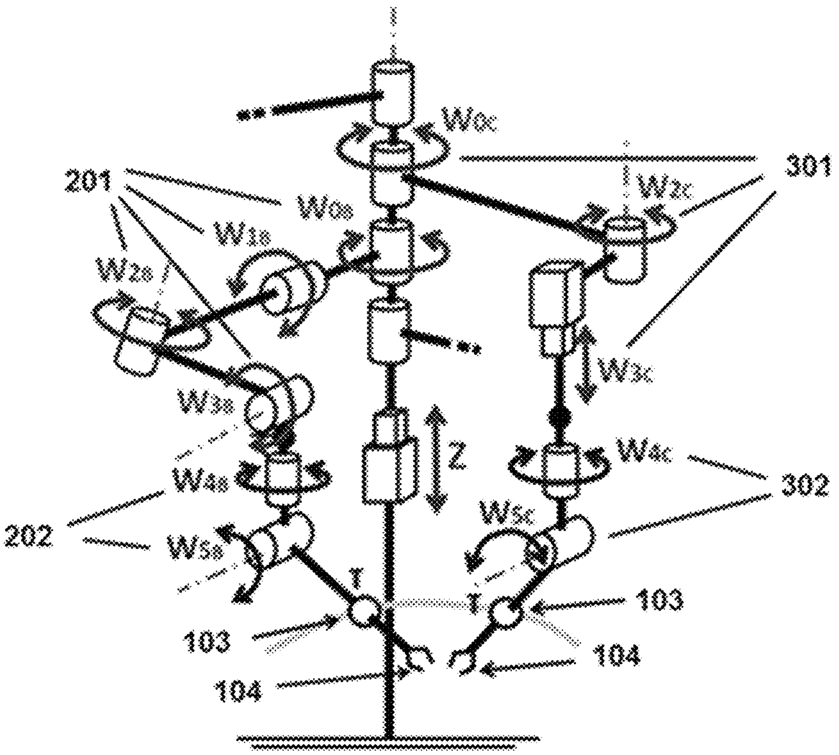
FIG. 3 illustrates in more detail the different joints of two of the robotic arms of a surgical robot.

FIG. 3 illustrates in more detail the architecture of the robotic arms 101 which are formed by poly-articulated chains. In particular, FIG. 3 shows the configuration of two of the robotic arms 101 of the surgical robot 100 (the other two arms have not been illustrated for the sake of simplicity of the figure). One of the robotic arms 101 is formed by joints 201 (referring to angles $W_{0B}$, $W_{1B}$, $W_{2B}$, and $W_3$B) and 202 (referring to angles $W_{4B}$ and $W_{5B}$), whereas the other arm is formed by joints 301 (referring to angles $W_{0c}$, $W_{2c}$, and $W_{3c}$) and 302 (referring to angles $W_{4c}$ and $W_{5c}$), given that the robotic arms 101 can have different architectures/designs for fixing their movements in space. Likewise, since the robotic arms 101 have different architectures, interferences between them are minimized. The duly motor-operated joints 201, 301 allow moving the support of the surgical instruments 102 in 3D space.

Figure 4:
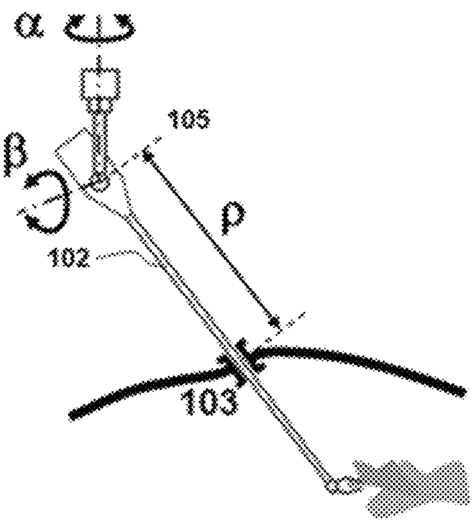
FIG. 4 graphically depicts the angles of orientation $\alpha$ and $\beta$ of the axes of rotation of the passive joints, and the parameter $\rho$ relative to the distance between the point of intersection of the axes of rotation of the passive joints and the fulcrum point.
Figure 5:
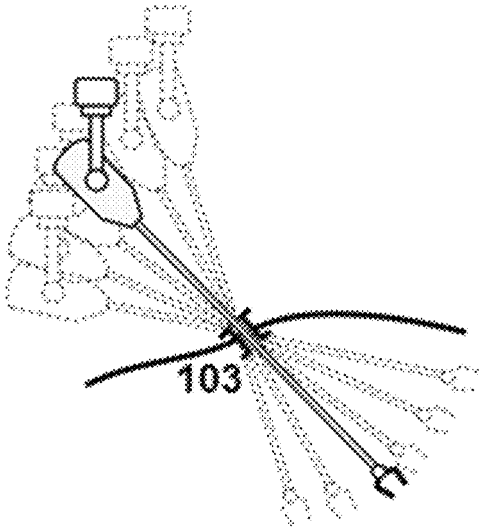
FIG. 5 shows an example of the movement of the trocar in the abdominal cavity.

Joints 202, 302 are passive, particularly cardan-type joints. Therefore, the position of the trocar 103 is not determined since parameter ρ (see FIG. 4) is not defined, which prevents performing calculation of the position of the surgical instrument 102 in the abdominal cavity. The calculation of parameter ρ can be performed geometrically from different positions of the robotic arm 101, taking into account that the orientations of angles α and β from the different points converge at a fixed point of the trocar 103 (see FIG. 5). In practice, these theoretical solutions could not provide sufficiently precise results given that the data (i.e., the variation of the angles of orientation α and β) is very small and the resolution of the angular sensors used for measuring said angles is limited. To achieve more precise results, the present invention performs, by means of the mentioned control unit, a recurrent calculation to perform an estimation and correction of the mentioned parameter ρ. To that end, based on an initial position $\rho_0$ there is performed, for each of the positions of movement of the robotic arms 101 for a specific time interval, a positive or negative correction of this magnitude in each performed movement according to the sign of the error observed in the comparison of the angles of orientation α and β. When correction is performed a large number of times per second at a high speed, the value of the increments of parameter ρ is statistically filtered/estimated.

If the estimation of p were correct, the line in space defined from the center of rotation in the direction in space defined by the angles of orientation α and β obtained by the sensors arranged in each robotic arm 101 would pass through the fulcrum point. A negative estimation error of distance p will cause a smaller variation of angles α and β than expected, whereas a positive estimation error will cause a greater variation of angles α and β than expected. The system can thereby perform kinematic calculations for controlling the position of the surgical instrument 102 inside the abdominal cavity by continuously updating the estimation of the position of the fulcrum point of the trocar 103, and ensuring that the stresses the robotic arms 101 exert on the trocar 103 are null, since the passive orienting joints 202, 302 are passive joints.

In a particular embodiment, the mentioned correction is not in the numerical algebraic form, but rather by means of a fuzzy logic algorithm, considering not the numerical value of the angles of orientation α and β, but rather the positive or negative deviation thereof between the values of these two angular orientations measured after each traveled interval and the orientations that they should have had in the absence of the movement of the trocar 103.

In one embodiment, the parameter ρ is estimated based on the variation of angles α and β when an elevational movement of the trocar 103 occurs, for example, due to a change in gas pressure, and if no movement whatsoever is performed through the controls 111 of the command station 110.

Figure 6:
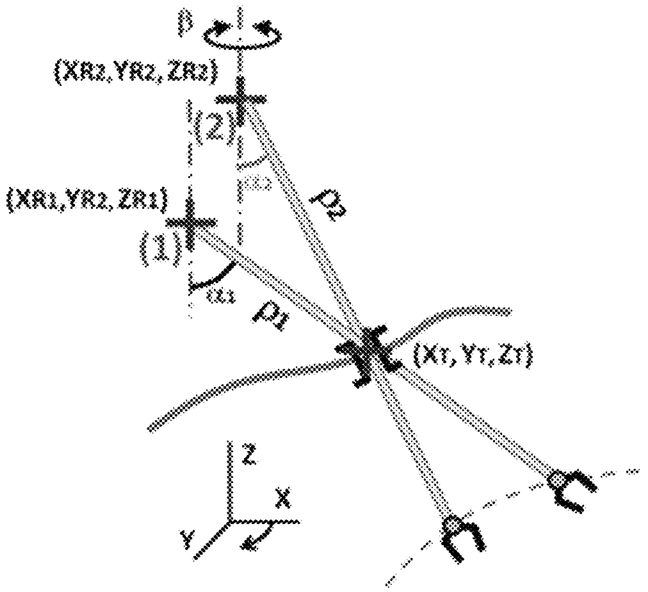
FIG. 6 graphically illustrates how the angles of orientation $\alpha$ and $\beta$ and the parameter $\rho$ for two robotic arms of a surgical robot are obtained, according to an embodiment.

An embodiment of the algorithm for calculating the dynamic correction of the value of the parameter ρ when one of the surgical arms 101 is moved from a first point (1) to a second point (2) is described in detail below, see FIG. 6:

According to this embodiment, the initial starting conditions of the algorithm are coordinates $X_T$, $Y_T$, $Z_T$ of the trocar 103 which have been calculated in an initial penetration by means of:

$$\begin{cases} XT_0 = XR_0 + \rho_0(t)\cdot\sin\alpha_{1t}\cdot\cos\beta_{1t} \\ YT_0 = YR_0 + \rho_0(t)\cdot\sin\alpha_{1t}\cdot\sin\beta_{1t} \\ ZT_0 = ZR_0 + \rho_0(t)\cdot\cos\alpha_{1t} \end{cases}$$

The preceding initial conditions are recursively operated in each new interval of movement. In position (1) of the robotic arm 101, the coordinates of the trocar 103 of the preceding point ($X_{T1}$, $Y_{T1}$, $Z_{T1}$), and the preceding value ρ(t−1) of the parameter ρ are available.

Next, the calculation of the angles of orientation α and β that should be had when reaching the second point is performed, after performing the travel interval from the first point to the second point if the estimated value ρ(t−1) were the correct one and the trocar 103 remains in its position.

$$\begin{cases} \alpha_{c2} = \operatorname{arc} tg\dfrac{\left((XT_1 - XR_2)^2 + (YT_1 - YR_2)^2\right)^{1/2}}{ZT - ZR_2} \\ \beta_{c2} = \operatorname{arc} tg\dfrac{YT_1 - YR_2}{XT_1 - XR_2} \end{cases}$$

The theoretical distance to the trocar ρ(t) from the position of the robotic arm 101 at the second point is then calculated:

$$\{\rho_2 = ((XT_1 - XR_2)^2 + (YT_1 - YR_2)^2)^{1/2}$$

At this second point, the new theoretical position of the trocar 103 viewed from the second point is calculated from the new previously calculated distance $\rho_2$:

$$\begin{cases} XT2 = XR2 + \rho 2(t) \cdot \sin\alpha_2 t \cdot \cos\beta_2 t \\ YT2 = YR2 + \rho 2(t) \cdot \sin\alpha_2 t \cdot \sin\beta_2 t \\ ZT2 = ZR2 + \rho 2(t) \cdot \cos\alpha_2 t \end{cases}$$

Finally, a reiterative correction of the obtained value ρ2 is performed based on the error between the values of the previously calculated angles αc2 and βc2 and the angles om and βm actually measured by the sensors, applying a fuzzy logic criterion, based on the sign of the error obtained and on the estimation of how big or small said error is:

$$\begin{cases} \text{If } (\alpha_{m2} > \alpha_{c2}) \text{ and } (\beta_{m2} > \alpha_{m2}) \\ \quad \rho 2(t+1) = \rho 2(t) + n \\ \text{If } (\alpha_{m2} > \alpha_{c2}) \text{ and } (\beta_{m2} > \alpha_{m2}) \\ \quad \rho 2(t+1) = \rho 2(t) - n \\ \text{If } |\alpha_{m2} - \alpha_{c2}| \text{ or } |\beta_{m2} \cdot \alpha_{m2}| < k \\ \quad n = 1 \\ \text{If } |\alpha_{m2} - \alpha_{c2}| \text{ or } |\beta_{m2} \cdot \alpha_{m2}| \geq k \\ \quad n = 2 \end{cases}$$

In this case, the increase or decrease of the calculated value of distance ρ can be n=1 or n=2, among other values, depending on if the obtained error is "small" or "big".

That is, once the distance to the trocar ρ(t) is determined/calculated (i.e. the distance between the intersection point of the axes of rotation of the passive orienting joints 202, 302 and the fulcrum point), after each iteration, the position of the trocar 103 can be particularly obtained by applying the following expressions:

$$\begin{cases} XT = XR + \rho \cdot \sin\alpha \cdot \cos\beta \\ YT = YR + \rho \cdot \sin\alpha \cdot \sin\beta \\ ZT = ZR + \rho \cdot \cos\alpha \end{cases}$$

where ($X_R$, $Y_R$, $Z_R$) are the coordinates of the securing points 105 (see FIG. 4), and α and β are the angles of orientation (i.e. angular values) of the passive orienting joints 202, 302 at the time of updating the trocar position ($X_T$, $Y_T$, $Z_T$).

The proposed invention can be implemented in hardware, software, firmware, or any combination thereof. If it is implemented in software, the functions can be stored in or coded as one or more instructions or code in a computer-readable medium.

The scope of the present invention is defined in the attached claims.

The invention claimed is:

1. An adaptive robot-assisted system for evaluating the position of a trocar in a robot-assisted laparoscopic surgery intervention, the system comprising:

a surgical robot comprising at least one robotic arm;

the robotic arm comprising a series of joints and configured for securing, by means of passive joints of the series of joints, a surgical instrument, each of the passive joints being non-motor operated cardan type joints configured for rotating freely, without the application of resistant torque by the surgical robot, guided by the surgical instrument held thereby about a point of intersection common to several axes of rotation, and the surgical instrument being adapted for being coupled to the trocar, the trocar being adapted for its introduction in the abdominal cavity of a patient during a laparoscopic surgery intervention;

a control unit comprising a processing unit with one or more processors and peripherals configured for controlling movements in the at least one robotic arm;

a command station configured for a teleoperated manipulation of the surgical robot through control elements, the control unit operatively connected to the command station; and a plurality of sensors arranged in the robotic arm and configured for measuring angles of orientation α and β of the axes of rotation of the passive joints;

the control unit being further configured for performing a dynamic estimation of the position of the trocar inserted in the wall of the abdominal cavity by performing the following steps:

comparing, for each of the movements of the surgical instrument in the abdominal cavity established during a specific time interval during the laparoscopic surgery intervention, the angles of orientation α and β measured by the plurality of sensors with theoretical angles of orientation α and β corresponding to an absence of movement of the trocar; and performing a correction of a parameter ρ, corresponding to a distance between a point of intersection of the axes of rotation of the passive joints and a fulcrum point corresponding to a previously estimated position of the fulcrum point, by positively or negatively increasing the parameter ρ in each of the movements during the specific time interval according to a sign value of an error obtained in the comparison.

2. The system according to claim 1, wherein the correction comprises applying a fuzzy logic algorithm based on a sign of the error obtained in the comparison and on an estimation of a magnitude of the error.

3. The system according to claim 1, wherein the plurality of control elements comprises at least one of pedals and actuators/push buttons.

4. The system according to claim 1, wherein the control unit is arranged inside the surgical robot.

5. The system according to claim 1, wherein the control unit is a remote control unit with respect to the surgical robot and the command station; the control unit being connected thereto with a cable or a wireless connection.

6. An adaptive method for evaluating the position of a trocar in a robot-assisted laparoscopic surgery intervention, the method comprising performing, using a control unit, comprising a processing unit with one or more processors and peripherals, controlling movements of at least one robotic arm of a surgical robot, the robotic arm comprising motor-operated joints for positioning a surgical instrument in space and passive non-motor operated cardan type joints configured for rotating freely without application of resistant torque by the robot and guided by the surgical instrument held thereby about a point of intersection common to several axes of rotation, a dynamic estimation of the position of at least one trocar inserted in a wall of the abdominal cavity of a patient, the trocar supporting a surgical instrument secured to the robotic arm, by performing the following steps:

comparing, for each of the movements of the surgical instrument in the abdominal cavity established during a specific time interval during a laparoscopic surgery intervention, previously measured angles of orientation α and β of axes of rotation of passive joints of the robotic arm with theoretical angles of orientation α and β corresponding to an absence of movement of the trocar, the measured angles of orientation α and β and the theoretical angles of orientation α and β being stored in a memory or database; and performing a correction of a parameter ρ, corresponding to a distance between a point of intersection of the axes of rotation of the passive joints and a fulcrum point corresponding to a previously estimated position of the fulcrum point, by positively or negatively increasing the parameter ρ in each of the movements during the specific time interval according to a sign value of an error obtained in the comparison, the correction being recursively performed to continuously update the estimation of the fulcrum point position.

7. The method according to claim 6, wherein the correction comprises applying a fuzzy logic algorithm based on the sign of the error and on an estimation of a magnitude of the error.

* * * * *